United States Patent [19]

Sato et al.

[11] Patent Number: 5,750,292
[45] Date of Patent: May 12, 1998

[54] ULTRAVIOLET ABSORBER PRECURSOR COMPOUND, PHOTOSENSITIVE RESIN COMPOSITION COMPRISING THE SAME AND IMAGE FORMING PROCESS

[75] Inventors: Morimasa Sato; Takekatsu Sugiyama, both of Shizuoka, Japan

[73] Assignee: Fuji Photo Film Co., Ltd., Kanagawa, Japan

[21] Appl. No.: 676,837

[22] Filed: Jul. 8, 1996

[30] Foreign Application Priority Data

Jul. 11, 1995 [JP] Japan .................................. 7-174860

[51] Int. Cl.$^6$ .......................... G03C 3/00; C07D 251/00
[52] U.S. Cl. .................. 430/15; 430/17; 430/18; 430/350; 430/270.1; 430/512; 522/78; 544/180
[58] Field of Search .................. 430/15, 17, 270.1, 430/350; 522/78; 544/180

[56] References Cited

U.S. PATENT DOCUMENTS

| | | | |
|---|---|---|---|
| 2,714,057 | 7/1955 | Chenicek | 544/180 |
| 3,203,550 | 8/1965 | Schaefer | 544/180 |
| 3,294,798 | 12/1966 | Schaefer | 544/180 |
| 3,344,137 | 9/1967 | Bader | 544/180 |
| 4,963,160 | 10/1990 | Hung et al. | 544/180 |
| 5,084,372 | 1/1992 | Hsieh et al. | 430/350 |
| 5,098,445 | 3/1992 | Hung et al. | 544/180 |
| 5,538,840 | 7/1996 | Toan et al. | 430/512 |
| 5,647,668 | 7/1997 | Hagemann et al. | 430/512 |

*Primary Examiner*—Roland Martin
*Attorney, Agent, or Firm*—Sughrue, Mion, Zinn, Macpeak & Seas, PLLC

[57] ABSTRACT

A compound represented by the following general formula (1) and a photosensitive resin composition comprising the compound of formula (1):

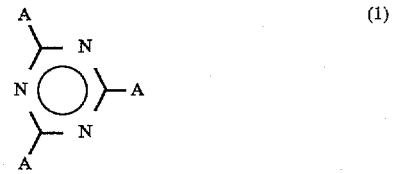

(1)

The compound of formula (1) normally has a low ultraviolet absorption, but has a high ultraviolet absorption when heat-treated. The present invention also provides a photosensitive resin layer composition which has a low ultraviolet absorption in an appropriate wavelength range such that ultraviolet rays reach sufficiently deep into the film to effect curing when exposed to light, but which has a high ultraviolet absorption when subsequently processed.

20 Claims, No Drawings

ULTRAVIOLET ABSORBER PRECURSOR COMPOUND, PHOTOSENSITIVE RESIN COMPOSITION COMPRISING THE SAME AND IMAGE FORMING PROCESS

FIELD OF THE INVENTION

The present invention relates to an ultraviolet absorber precursor compound, a photosensitive resin composition comprising the ultraviolet absorber precursor and an image forming process using the photosensitive resin composition. A multi-color image formed by the process of the present invention is particularly useful for preparing a color filter adapted for liquid crystal display, etc.

BACKGROUND OF THE INVENTION

A color filter adapted for a full-color liquid crystal display normally comprises a light-shielding pixel pattern provided between R, G and B pixels to prevent light leakage and to enhance contrast. The light-shielding pixel pattern is formed by a film made of metal such as chromium and the like or a dispersion of a black colorant in a photosensitive resin. In the case of a metal film such as chromium, the metal film is vacuum-evaporated onto the entire surface of a glass substrate. A resist pattern is then formed on the metal film. The exposed metal film is then etched to leave a patterned film. However, this process is disadvantageous in that it requires a very complicated procedure that results in a reduced yield and adds to the production cost.

A solution to the above described problems has previously been proposed which comprises the use of a photosensitive black resin comprising a photosensitive resin and carbon in combination to form a pattern of light-shielding pixels. In this technique, a film thickness of several micrometers is required to obtain light shielding properties. However, the light-shielding pixel pattern and the R, G and B pixels of the color filter should normally overlap to some extent to reduce sensitivity to alignment error. Consequently, surface roughness of the resulting color filter is unavoidable. Thus, from a practical standpoint, a leveling layer is provided on the color filter or the color filter is polished to obtain a level surface.

A technique for enhancing the surface flatness of the color filter is proposed in JP-A-3-209203 (The term "JP-A" as used herein means an "unexamined published Japanese patent application") and JP-A-4-69602. This technique is a self-aligning process which comprises applying a black photosensitive resin layer to the entire surface of a substrate having R, G and B pixels formed thereon, and then exposing the laminate to light on the opposite side thereof using the R, G and B pixels as an exposure mask to form a light-shielding pixel pattern in the gaps between the R, G and B pixels. In this process, the light-shielding pixel pattern is preferably formed in a final step. However, this process is disadvantageous in that common R, G and B colorants transmit considerable light in the ultraviolet region. Thus, the black photosensitive resin composition on the R, G and B pixels partially cures to remain.

A solution to the above described problem is proposed in JP-A-62-254103, JP-A-62-9301, JP-A-1-145626, JP-A-2-77014, and JP-A-7-225313. The subject technique comprises incorporating an ultraviolet absorber into the R, G and B pixels or impregnating these pixels with the ultraviolet absorber to enhance the ultraviolet shielding properties thereof when opposite side of the laminate is exposed to light. The ultraviolet absorber may be a benzotriazole compound, a compound described in JP-A-5-232630 or the like. However, this process is disadvantageous in that the ultraviolet absorber also absorbs exposure energy when forming the R, G and B pixel pattern. Consequently, the resin film cannot be completely exposed to light throughout the entire thickness thereof. This results in peeling or a loss of R, G and B pixels during development. This process is also disadvantageous in that the ultraviolet absorber has insufficient heat resistance. Thus, the ultraviolet absorber can volatilize or decompose when heated each time the pixels are formed such that the material exhibits reduced ultraviolet absorption.

SUMMARY OF THE INVENTION

It is therefore an object of the present invention to provide a compound which normally has a low ultraviolet absorption but which has a high ultraviolet absorption when heat-treated.

It is another object of the present invention to provide a photosensitive resin composition which receives ultraviolet rays deep within a film thereof to undergo curing when exposed to light, and which is subsequently processed to increase its ultraviolet absorption so that the film can serve as a self-alignment mask or can be used for other purposes.

These and other objects of the present invention will become more apparent from the following detailed description and Examples.

The above described objects of the present invention are accomplished by providing a photosensitive resin composition comprising a compound represented by the following general formula (1):

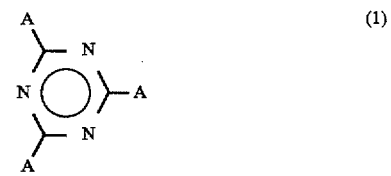

wherein A represents a group represented by the following general formula (2):

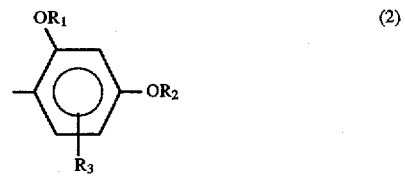

wherein $R_1$ represents a substituted or unsubstituted alkylcarbonyl group, a substituted or unsubstituted aralkylcarbonyl group, a substituted or unsubstituted arylcarbonyl group or a substituted or unsubstituted alkoxycarbonyl group; $R_2$ represents a hydrogen atom, a substituted or unsubstituted alkylcarbonyl group, a substituted or unsubstituted aralkylcarbonyl group, a substituted or unsubstituted arylcarbonyl group or a substituted or unsubstituted alkoxycarbonyl group; and $R_3$ represents a hydrogen atom or a lower alkyl group having generally from 1 to 15 carbon atoms, preferably from 1 to 7 carbon atoms.

The number of carbon atoms in the above described alkyl group, aralkyl group, aryl group or alkoxy group, excluding carbon atoms of the carbonyl group, is preferably from 1 to 15, particularly from 1 to 7. Preferred examples of substituents of the substituted alkylcarbonyl group, aralkylcarbonyl group, arylcarbonyl group and alkoxycarbonyl group include a halogen atom, a hydroxyl group, a lower alkyloxy group and an aryloxy group, the lower alkyloxy group and the aryloxy group generally having from 1 to 15 carbon atoms, preferably from 1 to 7 carbon atoms.

DETAILED DESCRIPTION OF THE INVENTION

The compound of formula (1) normally has a relatively low ultraviolet absorption but can serve as an ultraviolet absorber when subjected to heat treatment. The compound of formula (1) is hereinafter referred to as "ultraviolet absorber precursor".

Specific examples of the ultraviolet absorber precursor represented by general formula (1) are given below, but the present invention should not be construed as being limited thereto.

an azide compound and a binder, and a cinnamic photosensitive resin composition. Furthermore, a positive-working photosensitive resin composition comprising a phenolic resin and a quinonediazide compound may be used. Particularly preferred among these photosensitive resin compositions is a photopolymerizable resin composition.

The photopolymerizable resin composition comprises a photopolymerization initiator, a photopolymerizable monomer and a binder as basic constituents. These basic constituents are described in greater detail below.

The binder is preferably a compound which has good pigment dispersibility, good compatibility with the monomer and photopolymerization initiator, suitable alkaline developer solubility, suitable organic solvent solubility during preparation of the coating solution, good strength and an appropriate softening temperature.

| | Exemplary compounds | | |
|---|---|---|---|
| | $R_1$ | $R_2$ | $R_3$ |
| 1 | $-COCH_3$ | $-COCH_3$ | H |
| 2 | $-COC_2H_5$ | $-COC_2H_5$ | H |
| 3 | $-COC_3H_7$ | $-COC_3H_7$ | H |
| 4 | $-COCH_2Cl$ | $-COCH_2Cl$ | H |
| 5 | 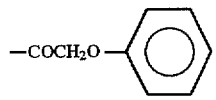 | 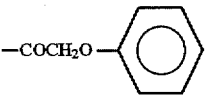 | H |
| 6 | 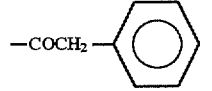 | 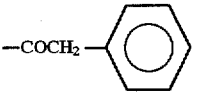 | H |
| 7 | 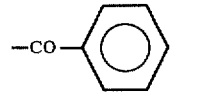 | 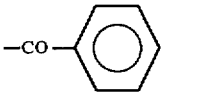 | H |
| 8 | 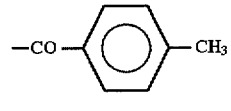 | 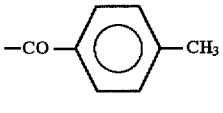 | H |
| 9 | $-COCH_2OCH_3$ | $-COCH_2OCH_3$ | H |
| 10 | $-CO-OCH_3$ | $-CO-OCH_3$ | H |
| 11 | $-CO-OC_2H_5$ | $-CO-OC_2H_5$ | H |
| 12 | $-CO-OC_3H_7$ | $-CO-OC_3H_7$ | H |
| 13 | $-COCH_3$ | $-COCH_3$ | 5-$CH_3$ |
| 14 | $-COCH_3$ | $-COCH_3$ | 5-$C_6H_{13}$ |
| 15 | $-CO-OCH_3$ | $-CO-OCH_3$ | 5-$CH_3$ |
| 16 | $-CO-OC(CH_3)_3$ | $-CO-OC(CH_3)_3$ | H |
| 17 | $-CO-OC(CH_3)_3$ | $-CO-OC(CH_3)_3$ | $CH_3$ |

The amount of the above described ultraviolet absorber precursor that is incorporated into the photosensitive resin composition is preferably from 0.1 to 30%, particularly preferably from 0.1 to 25%, based on the total solid content of the composition. Two or more different kinds of ultraviolet precursor compounds can be used in admixture.

The photosensitive resin composition of the present invention may be prepared by adding the ultraviolet absorber precursor represented by formula (1) to a known photosensitive resin composition. Examples of known photosensitive resin compositions employable herein include those disclosed in JP-A-3-282404. Specific examples of useful photosensitive resin compositions include a photosensitive resin composition comprising a negative-working diazo resin and a binder, a photopolymerizable resin composition, a photosensitive resin composition comprising Specific examples of useful binders include copolymers of (meth)acrylic acid and (meth)acrylic ester, styrene-maleic anhydride copolymers, and reaction product of these copolymers with an alcohol. Preferred among these compounds is a copolymer of (meth)acrylic acid and (meth)acrylic ester. The molecular weight of the binder is preferably from 5,000 to 20,000. The addition amount of the binder is preferably from 20% to 80% based on the total solid content of the resin composition.

Examples of useful monomers include known (meth)acrylic esters, urethane (meth)acrylates, (meth)acrylic amides, allyl compounds and vinyl esters as described in JP-A-60-258539. Preferred among these monomers is (meth)acrylic ester. The addition amount of the monomer is preferably from 10 to 60% by weight based on the total solid content of the photopolymerizable resin composition.

The photopolymerization initiator for use in the present invention preferably comprises at least one component having a molecular extinction coefficient of about 50 in the wavelength range of from about 300 to 500 nm. Examples of the photopolymerization initiator includes aromatic ketones, lophine dimer, benzoin, benzoinethers, polyhalogens and combinations of two or more of these compounds as disclosed in JP-A-2-48664, JP-A-1-152449 and JP-A-2-153353. Preferred examples of the photopolymerization initiators include the combination of 4,4'-bis(diethylamino) benzophenone and 2-(o-chlorophenyl)-4,5-diphenylimidazole dimer, and 4-[p-N,N-di (ethoxycarbonylmethyl)-2,6-di(trichloromethyl)-s-triazine]. The content of the photopolymerization initiator is preferably from 0.2 to 10% by weight based on the total solid content of the photopolymerizable resin composition.

The above described photopolymerizable resin composition may further comprise a colorant. The colorant may be a known dye or pigment, preferably a pigment from the standpoint of light resistance, heat resistance, chemical resistance, etc. Generally, the pigment grains are uniformly dispersed in the photosensitive resin layer to a diameter of preferably not more than 5 μm, particularly preferably not more than 1 μm. The pigment grains, if used in the preparation of a color filter, are preferably dispersed to a diameter of not more than 0.5 μm.

Specific examples of useful colorants include Victoria Pure Blue BO (C.I. 42595), Auramine (C.I. 41000), Fat Black HB (C.I. 26150), Monolight Yellow GT (C.I. Pigment Yellow 12), Permanent Yellow GR (C.I. Pigment Yellow 17), Permanent Yellow HR (C.I. Pigment Yellow 83), Permanent Carmine FBB (C.I. Pigment Red 146), Hostaperm Red E 5B (C.I. Pigment Violet 19), Permanent Rubine FBH (C.I. Pigment Red 11), Fast Pink B Spra (C.I. Pigment Red 81), Monastral Fast Blue (C.I. Pigment Blue 15), Monolite Fast Black B (C.I. Pigment Black 1), and carbon.

Further examples of preferred pigments are described below.

Preferred examples of useful yellow pigments include C.I. Pigment Yellow 20, C.I. Pigment Yellow 24, C.I. Pigment Yellow 83, C.I. Pigment Yellow 86, C.I. Pigment Yellow 93, C.I. Pigment Yellow 109, C.I. Pigment Yellow 110, C.I. Pigment Yellow 117, C.I. Pigment Yellow 125, C.I. Pigment Yellow 137, C.I. Pigment Yellow 138, C.I. Pigment Yellow 139, C.I. Pigment Yellow 147, C.I. Pigment Yellow 148, C.I. Pigment Yellow 153, C.I. Pigment Yellow 154, C.I. Pigment Yellow 166 and C.I. Pigment Yellow 168.

Preferred examples of useful orange pigments include C.I. Pigment Orange 36, C.I. Pigment Orange 43, C.I. Pigment Orange 51, C.I. Pigment Orange 55, C.I. Pigment Orange 59 and C.I. Pigment Orange 61.

Preferred examples of useful red pigments include C.I. Pigment Red 9, C.I. Pigment Red 97, C.I. Pigment Red 122, C.I. Pigment Red 123, C.I. Pigment Red 149, C.I. Pigment Red 168, C.I. Pigment Red 177, C.I. Pigment Red 180, C.I. Pigment Red 192, C.I. Pigment Red 215, C.I. Pigment Red 216, C.I. Pigment Red 217, C.I. Pigment Red 220, C.I. Pigment Red 223, C.I. Pigment Red 224, C.I. Pigment Red 226, C.I. Pigment Red 227, C.I. Pigment Red 228, C.I. Pigment Red 240 and C.I. Pigment Red 48:1.

Preferred examples of useful violet pigments include C.I. Pigment Violet 19, C.I. Pigment Violet 23, C.I. Pigment Violet 29, C.I. Pigment Violet 30, C.I. Pigment Violet 37, C.I. Pigment Violet 40 and C.I. Pigment Violet 50.

Preferred examples of useful blue pigments include C.I. Pigment Blue 15, C.I. Pigment Blue 15:6, C.I. Pigment Blue 22, C.I. Pigment Blue 60 and C.I. Pigment Blue 64.

Preferred examples of useful green pigments include C.I. Pigment Green 7 and C.I. Pigment Green 36.

Preferred examples of useful brown pigments include C.I. Pigment Brown 23, C.I. Pigment Brown 25 and C.I. Pigment Brown 26.

Preferred examples of useful black pigments include C.I. Pigment Black 7.

The above described colorants may be used singly or in admixture. The addition amount of the colorant is preferably from 2 to 70%, particularly from 5 to 50%, based on the total solid content of the resin composition.

The photosensitive resin composition may further comprise a solvent, examples of which include cellosolves such as ethylene glycol monomethyl ether, ethylene glycol monoethyl ether, propylene glycol monomethyl ether, propylene glycol monoethyl ether, diethylene glycol monomethyl ether and ethylene glycol monoethyl ether; ester acetates such as the acetic ester of the above noted cellosolves, ethyl acetate, n-propyl acetate, i-propyl acetate, n-butyl acetate and i-butyl acetate; aromatic hydrocarbons such as benzene, toluene and xylene; ketones such as methyl ethyl ketone, acetone, methyl isobutyl ketone and cyclohexane; and an alcohol such as ethanol, propanol, butanol, hexanol, cyclohexanol, ethylene glycol, diethylene glycol and glycerin, and other known dispersing aids and thermal polymerization inhibitors.

The image forming process of the present invention comprises at least the following steps 1 to 4:

1. providing the above described photosensitive resin composition on a substrate;
2. exposing the material to light through a desired photomask;
3. developing away unwanted areas to form pixels on the substrate; and
4. subjecting the pixels on the substrate to heat treatment.

The above described procedure comprising steps 1 to 4 can be repeated a plurality of times with photosensitive resin compositions comprising colorants having different hues to form a multi-color image.

The photosensitive resin composition may be applied to the substrate by a spin coating method, a roll coating method or the like, followed by drying. Alternatively, the photosensitive resin composition may be previously applied to a temporary support to form a layer transfer material which is then transferred to the substrate. The layer transfer process is particularly preferred from the standpoint of process stability, uniformity of film thickness, etc. Specific examples of the layer transfer material include a transfer material comprising a release layer which weakly adheres to the temporary support, and a photosensitive layer as disclosed in JP-A-4-208940; a photosensitive transfer material comprising a thermoplastic resin layer, an intermediate layer and a photosensitive resin layer provided on a temporary support, wherein the adhesion between the temporary support and the thermoplastic resin layer is smallest among the various layers as disclosed in JP-A-5-173320; a transfer material comprising a thermoplastic resin layer, a release layer and a photosensitive resin layer, wherein the adhesion between the thermoplastic resin layer and the release layer is smallest among the various layers as disclosed in JP-A-5-72724; and a photosensitive transfer material comprising a thermoplastic resin layer, an intermediate layer and a photosensitive resin layer provided on a temporary support, wherein the adhesion between the temporary support and the thermoplastic resin layer is smallest among the various layers as disclosed in JP-A-5-80503.

The photosensitive resin layer thus formed on the substrate is then patternwise exposed to light through a desired photomask. The light source for exposure may be a known light source such as an ultrahigh voltage mercury vapor lamp and a xenon lamp.

After patternwise exposure, the unwanted areas of the resin layer are then removed in a development step. The developer for use in this process may be a solvent or an alkaline aqueous solution which dissolves away the unexposed areas but does not dissolve away the exposed areas when a negative-working photosensitive resin is used. The developer may also be a solvent or an alkaline aqueous solution which dissolves away the exposed areas but does not dissolve away the unexposed areas when a positive-working photosensitive resin is used. With respect to recent environmental considerations, an alkaline aqueous type developer is advantageously used with both negative-working and positive-working photosensitive resins. For example, a dilute aqueous solution of an alkaline substance optionally containing a small amount of an organic solvent miscible with water may be used.

Examples of useful alkaline substances include hydroxides of an alkaline metal (e.g., sodium hydroxide, potassium hydroxide), carbonates of an alkaline metal (e.g., sodium carbonate, potassium carbonate), bicarbonates of an alkaline metal (e.g., sodium hydrogencarbonate, potassium hydrogencarbonate), silicates of an alkaline metal (e.g., sodium silicate, potassium silicate), metasilicates of an alkaline metal (e.g., sodium metasilicate, potassium metasilicate), triethanolamine, diethanolamine, monoethanolamine, morpholine, tetraalkylammonium hydroxides (e.g., tetramethylammonium hydroxide), and trisodium phosphate. The concentration of the alkaline substance in the aqueous solution is from 0.01 to 30% by weight. The pH value of the alkaline aqueous solution is preferably from 8 to 14.

Examples of the organic solvent miscible with water include methanol, ethanol, 2-propanol, 1-propanol, butanol, diacetone alcohol, ethylene glycol monomethyl ether, ethylene glycol monoethyl ether, ethylene glycol mono n-butyl ether, benzyl alcohol, acetone, methyl ethyl ketone, cyclohexanone, ε-caprolactone, γ-butyrolactone, dimethylformamide, dimethylacetamide, hexamethylphosphamide, ethyl lactate, methyl lactate, ε-caprolactam and N-methylpyrrolidone. The concentration of the organic solvent miscible with water is from 0.1 to 30% by weight.

The developer for use in the present invention may further comprise a known surface active agent. The concentration of the surface active agent is preferably from 0.01 to 10% by weight.

The developer may be used in the form of a bath or spray. In order to remove the unwanted areas from the photosensitive resin layer, the development process may be effected in combination with rubbing with a rotary brush or wet sponge in the developer. The temperature of the developer is preferably from about room temperature to 40° C. The development process may be followed by a rinsing step.

Subsequently, the material is subjected to heat treatment. In this heat treatment, the pixels are further cured. At the same time, the ultraviolet absorber precursor contained in the pixels decomposes to form an ultraviolet absorber. The heat treatment may be effected by means of a known heat treatment apparatus such as a convection oven, hot plate and infrared heater. The heat treatment is carried out such that the ultraviolet absorber precursor decomposes to exert its full effect of absorbing ultraviolet rays in the stage where this compound should be present as an ultraviolet absorber. The heat treatment temperature is preferably from 120° C. to 300° C., particularly preferably from 130° C. to 250° C. The heat treatment time is preferably from 1 minute to 200 minutes.

The ratio of the transmittancy of the unexposed photosensitive resin composition layer at 365 nm to that of the heat-treated photosensitive resin composition layer at 365 nm is preferably from 1:0.99 to 1:0.00001, more preferably from 1:0.5 to 1:0.00001, particularly preferably from 1:0.1 to 1:0.00001. The final transmittancy of the pixels thus heat-treated at 365 nm is preferably not more than 2%. If the final transmittancy exceeds 2%, the photosensitive resin composition layer cannot fully serve as a photomask in a self-alignment process.

The image forming process with a photosensitive layer transfer material is described in further detail below. If necessary, the cover sheet is removed from the photosensitive layer transfer material. The photosensitive resin layer is then laminated onto a substrate under pressure and heating. The lamination can be accomplished by means of a known laminator, vacuum laminator or the like. An auto cut laminator can be used to further enhance productivity. Thereafter, the temporary support is peeled. The material is exposed to light through a desired mask and then developed. Subsequently, the material is subjected to heat treatment under predetermined conditions. The exposure and development are effected in the same manner as described above.

The above procedure may be repeated a plurality of times with photosensitive layer transfer materials having differently colored photosensitive resin composition layers to form a multi-color image.

The multi-color image thus formed according to the process of the present invention can be used to prepare a color filter for a color liquid crystal display. The substrate of the color filter may be a known glass plate, a soda glass plate having a silicon oxide film formed thereon or the like.

A photosensitive resin composition free of colorant can be used as a protective layer for the color filter. The step of forming a protective layer may require patterning. During this process, the film is completely cured in the thickness direction. After heat treatment, a highly ultraviolet absorptive protective layer can be obtained to inhibit discoloration of the color filter due to back lighting or natural light.

A positive-working photosensitive resin composition can be used. In general, a positive-working photosensitive resin composition has a higher resolving power than a negative-working photosensitive resin composition. Thus, a positive-working photosensitive resin composition can be advantageously used for finer work. For example, a positive-working photosensitive resin composition comprising a novolak resin as a binder and a quinonediazide compound as a photosensitive material can be used which is well known in the field of microphotoresists for the production of IC's or printing plates. It is also known in the field of printing that the exposed areas of this type of composition become insoluble when heated. The composition can utilize this phenomenon to serve as a photosensitive resin composition for the production of B, G and R pixels.

The present invention will be further described in the following Examples, but the present invention should not be construed as being limited thereto. All parts are given by weight unless otherwise indicated.

SYNTHESIS EXAMPLE 1

Compound 1

To 300 ml of acetone were added 42.3 g (0.1 mol) of ground 2,4,6-tris(2,4-dihydroxyphenyl)-1,3,5-triazine monohydrate and 101 g (1 mol) of triethylamine. The interior of the reaction system was heated to a temperature of about 30° C. 79 g (1 mol) of acetyl chloride was then gradually added dropwise to the reaction system with stirring to effect a reaction. After completing the reaction, the reaction mixture was poured into ice water which had been weakly acidified with hydrochloric acid. As a result, Compound 1 crystallized. The crystal was then removed by filtration. (Yield: 56 g (85%)) The product was then recrystallized from a mixture of acetone and methanol. The compound thus obtained had a melting point of from 186° to 187° C. The compound exhibited $^1$H—NMR acetyl group peaks of δ2.06 ppm and δ2.33 ppm (in CDCl$_3$), and a λmax (in methanol) of 275 nm (ε48000).

SYNTHESIS EXAMPLE 2

Compound 10

The procedure of Synthesis Example 1 was followed to prepare Compound 10, except that methyl chloroformate was used in place of acetyl chloride (yield: 90%). The compound thus obtained had a melting point of from 153° to 154° C. The compound exhibited $^1$H—NMR acetyl group peaks of δ3.66 ppm and 3.95 ppm (in CDCl$_3$), and a λmax (in methanol) of 274 nm (ε49000).

EXAMPLES 1–17

A coating solution having the following formulation H1 was applied to a 75-μm thick polyethylene terephthalate temporary support, and then dried to provide a thermoplastic resin layer having a dry thickness of 20 μm.

| Thermoplastic resin layer formulation H1: | |
|---|---|
| Methyl methacrylate/2-ethylhexyl acrylate/benzyl methacrylate/ methacrylic acid copolymer (copolymerization ratio (molar ratio) = 55/30/10/5; weight-average molecular weight = 50,000) | 15.0 parts |
| Polypropylene glycol diacrylate (average molecular weight = 822) | 6.5 parts |
| Tetraethylene glycol dimethacrylate | 1.5 parts |
| p-Toluenesulfonamide | 0.5 parts |
| Benzophenone | 1.0 parts |
| Methyl ethyl ketone | 30.0 parts |

A coating solution having the following formulation B1 was applied to the above described thermoplastic resin layer, and then dried to provide a releasable intermediate layer having a dry thickness of 1.6 μm.

| Intermediate layer formulation B1: | |
|---|---|
| Polyvinyl alcohol (PVA205, available from Kuraray Co., Ltd.; Percent saponification: 80%) | 130 parts |
| Polyvinyl pyrrolidone (PVP K-90, available from GAF Corporation) | 60 parts |
| Fluorinic surface active agent (Surflon S-131, available from Asahi Glass Co., Ltd.) | 10 parts |
| Distilled water | 3,350 parts |

Coating solutions for red (R), blue (B), green (G) and black (B1) color photosensitive layers were prepared having the formulations set forth in Tables 1 and 2 below.

TABLE 1

Formulation of coating solutions for R, G and B color photosensitive layers

| | R layer | G layer | B layer |
|---|---|---|---|
| Benzyl methacrylate/methacrylic acid copolymer (molar ratio = 73/27; viscosity = 0.12) | 60.0 | 60.0 | 60.0 |
| Pentaerythritol tetraacrylate | 43.2 | 43.2 | 43.2 |
| Michler's ketone | 2.4 | 2.4 | 2.4 |
| 2-(o-Chlorophenyl)-diphenyl-imidazole dimer | 2.5 | 2.5 | 2.5 |
| Irgazin Red BPT (red) | 5.4 | — | — |
| Sudan Blue (blue) | — | 5.2 | — |
| Copper phthalocyanine (green) | — | — | 5.6 |
| Carbon black (black) | — | — | — |
| Methyl cellosolve acetate | 560 | 560 | 560 |
| Methyl ethyl ketone | 280 | 280 | 280 |

TABLE 2

Formulation of coating solution for B1 color photosensitive layer

| Benzyl methacrylate/methacrylic acid copolymer (molar ratio = 70/30; viscosity = 0.12) | 10.06 parts |
|---|---|
| Dipentaerythritol hexaacrylate | 10.60 parts |
| 2,4-Bis(trichloromethyl)-6-[4-(N,N-diethoxycarbomethyl)-3-bromophenyl]-S-triazine | 0.52 parts |
| Pigment Red 177 | 4.00 parts |
| Pigment Blue 15:6 | 2.86 parts |
| Pigment Yellow 139 | 2.27 parts |
| Pigment Violet 23 | 0.39 parts |
| Carbon Black | 1.70 parts |
| Hydroquinone monomethyl ether | 0.01 parts |
| F177P (surface active agent available from Dainippon Ink & Chemicals, Inc.) | 0.07 parts |
| Methyl cellosolve acetate | 40.00 parts |
| Methyl ethyl ketone | 125.0 parts |

To the coating solution for the R color layer were then added each of Compounds 1 to 17 as exemplified above in an amount of 10% in terms of solid content to prepare the coating solutions for the R color layer for use in Examples 1 to 17, respectively.

The above described coating solutions for the R color layer were, respectively, applied to the temporary supports comprising the above described thermoplastic resin layer and intermediate layer provided thereon, and then dried to form photosensitive resin layers each having a dry thickness of 2 μm. The R photosensitive resin layers thus obtained exhibited a transmittancy of 8% at 365 nm.

A polypropylene cover sheet (thickness: 12 μm) was then contact-bonded to the photosensitive resin layer to prepare a photosensitive transfer material.

The cover sheet was peeled off the R photosensitive transfer material comprising Compound 1. A 1.1-mm thick glass substrate and the R photosensitive transfer material were then laminated together under pressure (0.8 kg/cm$^2$) and heating (130° C.) by means of a laminator (VP-II, available from Taisei Laminator Co., Ltd.) such that the glass substrate was contacted with the photosensitive resin layer. Subsequently, the temporary support was stripped from the laminator at the interface with the thermoplastic resin layer. The laminate was then exposed to light from an ultrahigh mercury vapor lamp through a photomask at an exposure of 20 mj/cm$^2$. The laminate was then developed with a 1:10 (by weight) mixture of an alkaline developer (CD, available from Fuji Hunt Electronics Technology Co., Ltd.) and water to remove the uncured areas. Thus, an R pattern was formed. A comparison was made by increasing the development time by 5 seconds, 10 seconds, 15 seconds and 20 seconds. As a result, no missing pixels or other defects were observed. Thereafter, the laminate was subjected to heat treatment at a temperature of 220° C. for 20 minutes. The resulting R pixel exhibited a transmittancy of 0.5% at 365 nm. The ratio of the transmittancy of the unexposed photosensitive resin layer to that of the heat-treated photosensitive resin layer at 365 nm was 1:0.063. Subsequently, G and B pixels were similarly formed by G and B photosensitive transfer materials, respectively. Finally, using a self-aligning process, a black matrix was formed using the B1 photosensitive transfer material. Thus, a color filter was prepared. The transmittancy of the R pixel at 365 nm was low enough to allow the laminate to be exposed at an exposure of 100 mj/cm² on the opposite side there of. Thus, a sufficient exposure was attained. The resulting black matrix exhibited an optical density of not less than 2.3.

Similarly, color filters were prepared using the R photosensitive transfer materials comprising Compounds 2 to 17, respectively. In each case, no missing images or other defects were observed. As shown in Table 3, these pixels exhibited a sufficiently low transmittancy at 365 nm after heat treatment. The black matrix thus obtained exhibited an optical density of not less than 2.3.

TABLE 3

Ultraviolet transmittancy of pixel after heat treatment

| Compound No. | Transmittancy at 365 nm after heat treatment (%) |
| --- | --- |
| 1 | 0.5 |
| 2 | 0.6 |
| 3 | 0.6 |
| 4 | 0.7 |
| 5 | 0.6 |
| 6 | 0.8 |
| 7 | 0.9 |
| 8 | 0.6 |
| 9 | 0.8 |
| 10 | 0.5 |
| 11 | 0.7 |
| 12 | 0.6 |
| 13 | 0.6 |
| 14 | 0.8 |
| 15 | 0.9 |
| 16 | 0.6 |
| 17 | 0.7 |

COMPARATIVE EXAMPLE 1

An R pattern was formed in the same manner as in example 1, except that a coumarin compound (Sigenox 102, available from Hakkol Chemical Co., Ltd.) was used as the ultraviolet absorber in an amount such that the transmittancy at 365 nm was 0.5% when the film was dried. The transmittancy of the R pixel after heat treatment was 0.5%. The ratio of the transmittancy of the unexposed photosensitive resin layer to that of the exposed photosensitive resin layer at 365 nm was 1:1. The pixel thus obtained had sufficient ultraviolet shielding properties. However, because the exposure energy did not reach a sufficient depth in the film during patternwise exposure, pixel loss occurred when the development time was increased.

As discussed above, the ultraviolet absorber precursor of the present invention provides a photosensitive resin composition which, during image formation, hardly absorbs ultraviolet rays to allow for sufficient exposure deep within the film. Consequently, there is no pixel loss during development. However, after subsequent heat treatment, the resin composition absorbs ultraviolet rays to the extent that it is able to serve as a mask for image formation by a self-alignment process.

While the invention has been described in detail and with reference to specific embodiments thereof, it will be apparent to one skilled in the art that various changes and modifications can be made therein without departing from the spirit and scope thereof.

What is claimed is:

1. An ultraviolet absorber precursor compound represented by the following formula (1):

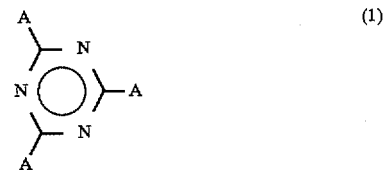

wherein A represents a group represented by the following formula (2):

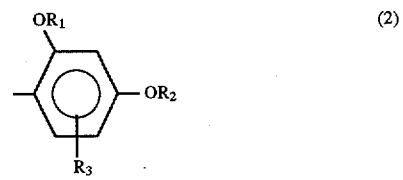

wherein $R_1$ represents a substituted or unsubstituted alkylcarbonyl, aralkylcarbonyl, arylcarbonyl or alkoxycarbonyl group; $R_2$ represents a hydrogen atom or a substituted or unsubstituted alkylcarbonyl, aralkylcarbonyl, arylcarbonyl or alkoxycarbonyl group; and $R_3$ represents a hydrogen atom or a lower alkyl group.

2. A photosensitive resin composition comprising an ultraviolet absorber precursor compound represented by the following formula (1):

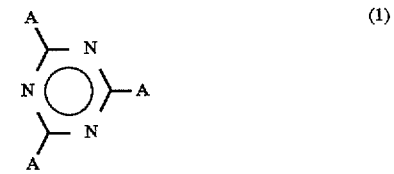

wherein A represents a group represented by the following formula (2):

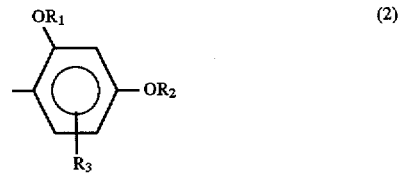

wherein $R_1$ represents a substituted or unsubstituted alkylcarbonyl, aralkylcarbonyl, arylcarbonyl or alkoxycarbonyl group; $R_2$ represents a hydrogen atom or a substituted or unsubstituted alkylcarbonyl, aralkylcarbonyl, arylcarbonyl or alkoxycarbonyl group; and $R_3$ represents a hydrogen atom or a lower alkyl group.

3. The photosensitive resin composition according to claim 2, wherein said photosensitive resin composition is a photopolymerizable composition comprising at least a binder, a photopolymerizable monomer and a photopolymerization initiator.

4. The photosensitive resin composition according to claim 2, further comprising a coloring agent.

5. The photosensitive resin composition according to claim 3, further comprising a coloring agent.

6. The photosensitive resin composition according to claim 4, wherein said coloring agent is a pigment.

7. The photosensitive resin composition according to claim 5, wherein said coloring agent is a pigment.

8. An image forming process, which comprises the steps of:
  (a) providing on a substrate a photosensitive resin layer composition comprising an ultraviolet absorber precursor compound represented by the following formula (1):

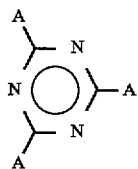

wherein A represents a group represented by the following formula (2):

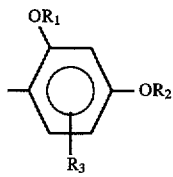

wherein $R_1$ represents a substituted or unsubstituted alkylcarbonyl, aralkylcarbonyl, arylcarbonyl or alkoxycarbonyl group; $R_2$ represents a hydrogen atom or a substituted or unsubstituted alkylcarbonyl, aralkylcarbonyl, arylcarbonyl or alkoxycarbonyl group; and $R_3$ represents a hydrogen atom or a lower alkyl group to prepare an image forming material;
  (b) exposing said photosensitive resin layer composition to light through a photomask;
  (c) developing the material to remove either the exposed or unexposed areas of the photosensitive resin layer to form picture elements on said substrate; and
  (d) heat-treating the picture elements formed on said substrate.

9. The image forming process according to claim 8, wherein said photosensitive resin composition is a photopolymerizable composition comprising at least a binder, a photopolymerizable monomer and a photopolymerization initiator.

10. The image forming process according to claim 8, wherein said photosensitive resin composition further comprises a coloring agent.

11. The image forming process according to claim 9, wherein said photosensitive resin composition further comprises a coloring agent.

12. The image forming process according to claim 10, wherein said coloring agent is a pigment.

13. The image forming process according to claim 11, wherein said coloring agent is a pigment.

14. The image forming process according to claim 8, wherein the ratio of the transmittancy of said photosensitive resin composition layer before step (b) to the transmittancy of the picture elements after step (d) at 365 nm is from 1:0.99 to 1:0.00001.

15. The image forming process according to claim 14, wherein the transmittancy of the picture elements after heat-treating is not more than 2% at 365 nm.

16. The image forming process according to claim 8, wherein the series of steps (a) to (d) is repeated at least twice.

17. A multi-color image, formed by a process comprising the steps of:
  (a) providing on a substrate a photosensitive resin layer composition comprising a coloring agent and an ultraviolet absorber precursor compound represented by the following formula (1):

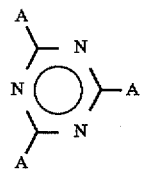

wherein A represents a group represented by the following formula (2):

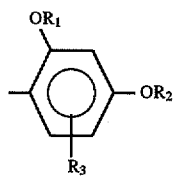

wherein $R_1$, represents a substituted or unsubstituted alkylcarbonyl, aralkylcarbonyl, arylcarbonyl or alkoxycarbonyl group; $R_2$ represents a hydrogen atom or a substituted or unsubstituted alkylcarbonyl, aralkylcarbonyl, arylcarbonyl or alkoxycarbonyl group; and $R_3$ represents a hydrogen atom or a lower alkyl group to prepare an image forming material;
  (b) exposing said photosensitive resin layer composition to light through a photomask;
  (c) developing the material to remove either the exposed or the unexposed areas of the photosensitive resin layer to form picture elements on said substrate;
  (d) heat-treating the picture elements formed on said substrate; and
  (e) repeating the series of steps (a) to (d) at least one time using a photosensitive resin composition comprising a coloring agent having a different hue.

18. The multi-color image according to claim 17, wherein said photosensitive resin composition is a photopolymerizable composition comprising at least a binder, a photopolymerizable monomer and a photopolymerization initiator.

19. The multi-color image according to claim 18, wherein said coloring agent is a pigment.

20. The multi-color image according to claim 19, wherein said coloring agent is a pigment.

* * * * *